(12) United States Patent
Tsujioka et al.

(10) Patent No.: US 6,407,232 B1
(45) Date of Patent: *Jun. 18, 2002

(54) IONIC METAL COMPLEX AND PROCESS FOR SYNTHESIZING SAME

(75) Inventors: Shoichi Tsujioka; Hironari Takase; Mikihiro Takahashi, all of Saitama (JP)

(73) Assignee: Central Glass Company, Limited, Ube (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/625,349

(22) Filed: Jul. 25, 2000

(30) Foreign Application Priority Data

Aug. 2, 1999 (JP) ............................................. 11-219045
Mar. 13, 2000 (JP) ........................................ 2000-069201

(51) Int. Cl.⁷ .................... C07D 279/00; C07D 279/04; C07D 273/00; C07D 409/00; C07D 493/00
(52) U.S. Cl. ................................ 544/54; 544/3; 544/5; 544/6; 544/64; 544/65; 544/97; 549/30; 549/210
(58) Field of Search ................................ 544/54, 97, 3, 544/5, 6, 64, 65; 549/30, 210

(56) References Cited

FOREIGN PATENT DOCUMENTS

EP 586235 * 9/1993

OTHER PUBLICATIONS

Redshaw et. al., CA 118:51168, 1993, (J. Chem. Soc., Dalton Trans.).*
Hasegawa et. al., CA 119:282228, 1993, (JP 05150555).*

Grant & Hackh's Chemical Dictionary, (c) 1987, McGraw–Hill, Inc., New York, NY, p.409,.*

* cited by examiner

Primary Examiner—Mukund J. Shah
Assistant Examiner—Tamthom N. Truong
(74) Attorney, Agent, or Firm—Crowell & Moring LLP

(57) ABSTRACT

The invention relates an ionic metal complex represented by the general formula (1):

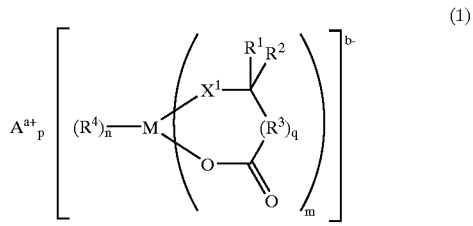

wherein M is an element of groups 3–15 of the periodic table; $A^{a+}$ represents a metal ion, onium ion or proton; $X^1$ represents O, S or $NR^5R^6$; each of $R^1$ and $R^2$ independently represents H, a halogen, a $C_1$–$C_{10}$ alkyl group or $C_1$–$C_{10}$ halogenated alkyl group; $R^3$ represents a $C_1$–$C_{10}$ alkylene group, $C_1$–$C_{10}$ halogenated alkylene group, $C_4$–$C_{20}$ aryl group or $C_4$–$C_{20}$ halogenated aryl group; $R^4$ represents a halogen, $C_1$–$C_{10}$ alkyl group, $C_1$–$C_{10}$ halogenated alkyl group, $C_4$–$C_{20}$ aryl group, $C_4$–$C_{20}$ halogenated aryl group or $X^2R^7$; $X^2$ represents O, S or $NR^5R^6$; each of $R^5$ and $R^6$ represents H or a $C_1$–$C_{10}$ alkyl group; and $R^7$ represents a $C_1$–$C_{10}$ alkyl group, $C_1$–$C_{10}$ halogenated alkyl group, $C_4$–$C_{20}$ aryl group or $C_4$–$C_{20}$ halogenated aryl group. The ionic metal complex can be used as a supporting electrolyte for electrochemical devices, a polymerization catalyst of polyolefins and so forth, or a catalyst for organic synthesis.

18 Claims, No Drawings

IONIC METAL COMPLEX AND PROCESS FOR SYNTHESIZING SAME

BACKGROUND OF THE INVENTION

The present invention relates to an ionic metal complex having a novel chemical structure and a process for synthesizing the ionic metal complex that is used as a supporting electrolyte for lithium batteries, lithium ion batteries, electrical double-layer capacitors and other electrochemical devices, a polymerization catalyst for polyolefins and so forth, or a catalyst for organic synthesis.

Ionic complexes, such as $PF_6^-$, $BF_4^-$ and $AsF_6^-$, formed by bonding of Lewis acids with F ion have been used in applications such as supporting electrolytes for electrochemical devices, polymerization catalysts for polyolefins and so forth or catalysts for organic synthesis due to their solubility and ion dissociation characteristics.

As the application range of these ionic complexes becomes increasingly diverse, efforts are being made to search for the optimum ionic complex for each application, and these ionic complexes are being required to have properties including heat resistance, hydrolysis resistance, low toxicity and recycleability.

SUMMARY OF THE INVENTION

It is an object of the present invention to provide a useful, novel, ionic metal complex and a process for synthesizing the same.

As a result of earnest studies, the inventors of the present invention found an ionic metal complex having a novel chemical structure and a process for synthesizing the same, thereby leading to completion of the present invention.

According to the present invention, there is provided an ionic metal complex represented by the general formula (1):

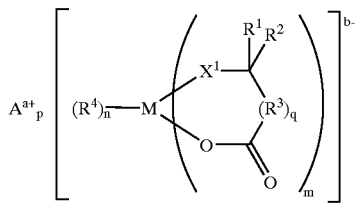

(1)

wherein M is a transition metal selected from the group consisting of elements of groups 3–11 of the periodic table, or an element selected from the group consisting of elements of groups 12–15 of the periodic table; $A^{a+}$ represents a metal ion, onium ion or proton; provided that M is not B when $A^{a+}$ is $Cs^+$; a represents a number from 1 to 3; b represents a number from 1 to 3; p is b/a; m represents a number from 1 to 3; n represents a number from 0 to 4; q is 0 or 1; $X^1$ represents O, S or $NR^5R^6$; each of $R^1$ and $R^2$ independently represents H, a halogen, a $C_1$–$C_{10}$ alkyl group or $C_1$–$C_{10}$ halogenated alkyl group; $R^3$ represents a $C_1$–$C_{10}$ alkylene group, $C_1$–$C_{10}$ halogenated alkylene group, $C_4$–$C_{20}$ aryl group or $C_4$–$C_{20}$ halogenated aryl group; $R^4$ represents a halogen, $C_1$–$C_{10}$ alkyl group, $C_1$–$C_{10}$ halogenated alkyl group, $C_4$–$C_{20}$ aryl group, $C_4$–$C_{20}$ halogenated aryl group or $X^2R^7$; $X^2$ represents O, S or $NR^5R^6$; each of $R^5$ and $R^6$ represents H or a $C_1$–$C_{10}$ alkyl group; and $R^7$ represents a $C_1$–$C_{10}$ alkyl group, $C_1$–$C_{10}$ halogenated alkyl group, $C_4$–$C_{20}$ aryl group or $C_4$–$C_{20}$ halogenated aryl group.

According to the present invention, there is provided a first process for synthesizing the ionic metal complex. The first process comprises reacting a compound represented by the general formula (2) with a metal complex represented by the general formula (3). This compound contains at least two active hydrogens.

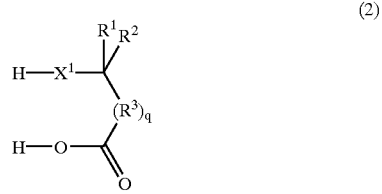

(2)

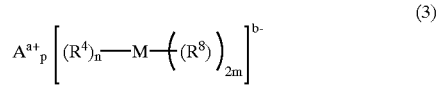

(3)

wherein $X^1$, $R^1$, $R^2$, $R^3$, $R^4$, M, $A^{a+}$, q, a, b, p, m, and n are defined as above, $R^8$ represents a halogen, hydroxyl group, hydrogen, $C_1$–$C_{10}$ alkyl group, $C_1$–$C_{10}$ halogenated alkyl group, $C_4$–$C_{20}$ aryl group, $C_4$–$C_{20}$ halogenated aryl group or $X^3R^9$; $X^3$ represents O, S or $NR^5R^6$ where $R^5$ and $R^6$ are defined as above; and $R^9$ represents a $C_1$–$C_{10}$ alkyl group, $C_1$–$C_{10}$ halogenated alkyl group, $C_4$–$C_{20}$ aryl group or $C_4$–$C_{20}$ halogenated aryl group.

According to the present invention, there is provided a second process for synthesizing the ionic metal complex. The second process comprises (a) reacting a first compound represented by the general formula (2) with a metal complex represented by the general formula (4), thereby obtaining an intermediate; and (b) reacting the intermediate with a second compound, thereby obtaining the ionic metal complex. The first compound contains at least two active hydrogens. The second compound contains a cation represented by $A^{a+}$ defined as above and is selected from the group consisting of metal halides, metal alkoxides, metal carboxylates, metal hydroxides, metal oxides, metal carbonates, quaternary alkylonium halides, quaternary alkylonium hydroxides and quaternary alkylonium carboxylates.

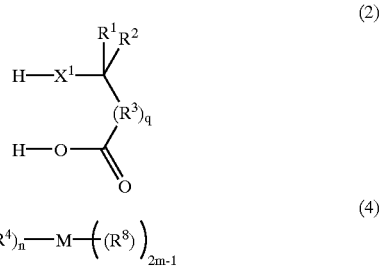

(2)

(4)

wherein $X^1$, $R^1$, $R^2$, $R^3$, $R^4$, $R^8$, M, q, m, and n are defined as above.

According to the present invention, there is provided a third process for synthesizing the ionic metal complex. The third process comprises (a) reacting a first compound represented by the general formula (2) with a second compound containing an alkali metal or alkali-earth metal, thereby obtaining an intermediate; and (b) reacting the intermediate with a metal complex represented by the general formula (5),

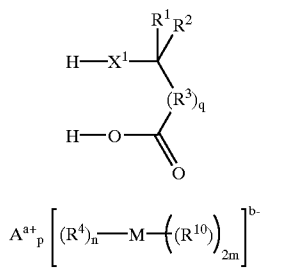

(2)

$$A^{a+}{}_p \left[ (R^4)_n-M-(R^{10})_{2m} \right]^{b-}$$ (5)

wherein $X^1$, $R^1$, $R^2$, $R^3$, $R^4$, M, $A^{a+}$, q, a, b, p, m, and n are defined as above, $R^{10}$ represents a halogen or hydroxyl group.

The above-mentioned ionic metal complex has a novel chemical structure and can be used as a supporting electrolyte for lithium batteries, lithium ion batteries, electrical double-layer capacitors and other electrochemical devices, a polymerization catalyst for polyolefins and so forth, or a catalyst for organic synthesis. The ionic metal complex can be synthesized by each of the above-mentioned first, second and third processes.

DESCRIPTION OF THE PREFERRED EMBODIMENTS

According to the invention, the alkyl groups, halogenated alkyl groups, aryl groups and halogenated aryl groups, which are contained in the ionic metal complex and the raw materials for synthesizing the same, may be branched and/or may have other functional groups such as hydroxyl groups and ether bonds.

The followings are specific nine examples of the ionic metal complex represented by the general formula (1) of the present

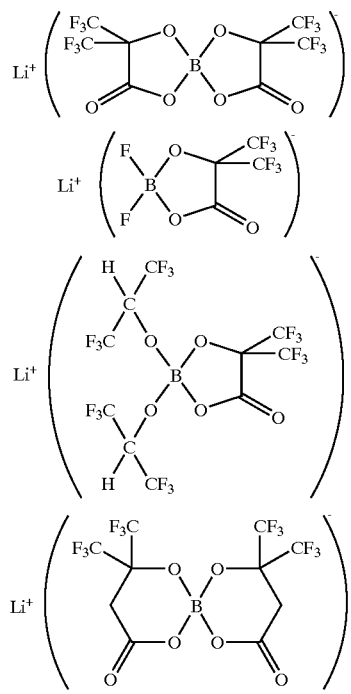

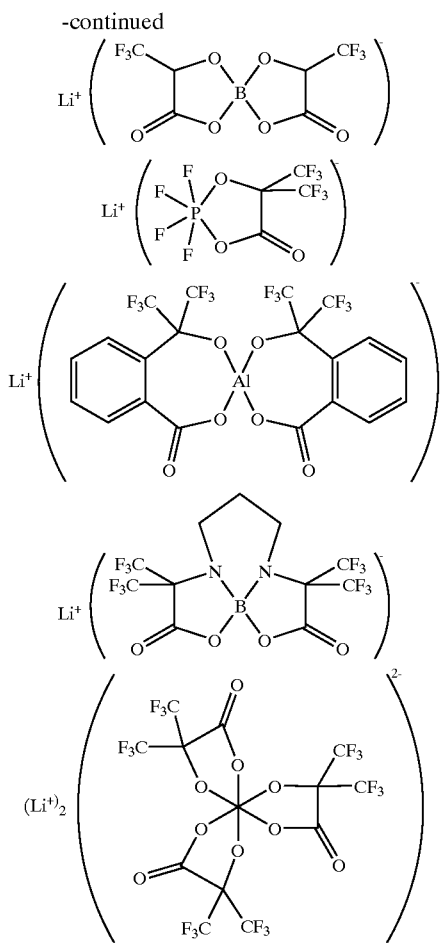

Here, although lithium ion is indicated as an example of $A^{a+}$ of the general formula (1), examples of other cations that can be used other than lithium ion include sodium ion, potassium ion, magnesium ion, calcium ion, barium ion, cesium ion, silver ion, zinc ion, copper ion, cobalt ion, iron ion, nickel ion, manganese ion, titanium ion, lead ion, chromium ion, vanadium ion, ruthenium ion, yttrium ion, lanthanoid ion, actinoid ion, tetrabutylammonium ion, tetraethylammonium ion, tetramethylammonium ion, triethylmethylammonium ion, triethylammonium ion, pyridinium ion, imidazolium ion, proton, tetraethylphosphonium ion, tetramethylphosphonium ion, tetraphenylphosphonium ion, triphenylsulfonium ion, triethylsulfonium ion and triphenylmethyl ion. In the case of considering the application of the ionic metal complex for electrochemical devices and the like, lithium ion, tetraalkylammonium ion and proton are preferable. In addition, in the case of the application of the ionic metal complex for catalyst, lithium ion, proton, triphenylmethyl ion, trialkylammonium ion and metallocenium ion are preferable. As shown in the general formula (1), the valency (valence) of the $A^{a+}$ cation is preferably from 1 to 3. If the valency is larger than 3, the problem occurs in which it becomes difficult to dissolve the ionic metal complex in solvent due to the increase in crystal lattice energy. Consequently, in the case of requiring solubility of the ionic metal complex, a valency of 1 is preferable. As shown in the general formula (1), the valency (b−) of the anion is similarly preferably from 1 to 3, and a valency of 1 is particularly preferable.

The constant p expresses the ratio of the valency of the anion to the valency of the cation, namely b/a.

In the general formula (1), M at the center of the ionic metal complex of the present invention is selected from elements of groups 3–15 of the periodic table. It is preferably Al, B, V, Ti, Si, Zr, Ge, Sn, Cu, Y, Zn, Ga, Nb, Ta, Bi, P, As, Sc, Hf or Sb, and more preferably Al, B or P. Although it is possible to use various elements for the M other than these preferable examples, synthesis is relatively easy in the case of using Al, B, V, Ti, Si, Zr, Ge, Sn, Cu, Y, Zn, Ga, Nb, Ta, Bi, P, As, Sc, Hf or Sb. In addition to ease of synthesis, the ionic metal complex has excellent properties in terms of low toxicity, stability and production cost in the case of using Al, B or P.

In the general formula (1), the organic or inorganic portion bonded to M is referred to as the ligand. As mentioned above, $X^1$ in the general formula (1) represents O, S or $NR^5R^6$, and is bonded to M through its hetero atom (O, S or N). Although the bonding of an atom other than O, S or N is not impossible, the synthesis becomes extremely bothersome. The ionic metal complex represented by the general formula (1) is characterized by these ligands forming a chelate structure with M since there is bonding with M by a carboxyl group (—COO—) other than $X^1$ within the same ligand. As a result of this chlelation, the heat resistance, chemical stability and hydrolysis resistance of the ionic metal complex are improved. Although constant q in this ligand is either 0 or 1, in the case of 0 in particular, since the chelate ring becomes a five-member ring, chelating effects are demonstrated most prominently, making this preferable due to the resulting increase in stability. In addition, since the negative charge of the central M is dissipated by electron attracting effects of the carboxyl group(s) resulting in an increase in electrical stability of the anion, ion dissociation becomes extremely easy resulting in corresponding increases of the ionic metal complex in solvent solubility, ion conductivity, catalyst activity and so forth. In addition, the other properties of heat resistance, chemical stability and hydrolysis resistance are also improved.

In the general formula (1), each of $R^1$ and $R^2$ is independently selected from H, halogen, $C_1$–$C_{10}$ alkyl groups and $C_1$–$C_{10}$ halogenated alkyl groups. At least one of either $R^1$ and $R^2$ is preferably a fluorinated alkyl group, and more preferably, at least one of $R^1$ and $R^2$ is a trifluoromethyl group. Due to the presence of an electron-attracting halogen and/or a halogenated alkyl group for $R^1$ and $R^2$, the negative charge of the central M is dissipated. This results in an increase of the anion of the general formula (1) in electrical stability. With this, the ion dissociation becomes extremely easy resulting in an increase of the ionic metal complex in solvent solubility, ion conductivity, catalyst activity and so forth. In addition, other properties of heat resistance, chemical stability and hydrolysis resistance are also improved. The case in which the halogen is fluorine in particular has significant advantageous effects, while the case of a trifluoromethyl group has the greatest advantageous effect.

In the general formula (1), R3 is selected from $C_1$–$C_{10}$ alkylene groups, $C_1$–$C_{10}$ halogenated alkylene groups, $C_4$–$C_{20}$ aryl groups and $C_4$–$C_{20}$ halogenated aryl groups. $R^3$ is preferably one which forms a 5 to 10-membered ring when a chelate ring is formed with the central M. The case of a ring having more than 10 members is not preferable, since chelating advantageous effects are reduced. In addition, in the case $R^3$ has a portion of hydroxyl group or carboxyl group, it is possible to form a bond between the central M and this portion.

In the general formula (1), $R^4$ is selected from halogens, $C_1$–$C_{10}$ alkyl groups, $C_1$–$C_{10}$ halogenated alkyl groups, $C_4$–$C_{20}$ aryl groups, $C_4$–$C_{20}$ halogenated aryl groups and $X^2R^7$. Of these, fluorine is preferable. $X^2$ represents O, S or $NR^5R^6$ and bonds to M through one of these heteroatoms (O, S and N). Although the bonding of an atom other than O, S or N is not impossible, the synthesis becomes extremely bothersome. Each of $R^5$ and $R^6$ is selected from H and $C_1$–$C_{10}$ alkyl groups. Each of $R^5$ and $R^6$ differs from other groups (e.g., $R^1$ and $R^2$) in that the former is not required to be an electron attracting group. In the case of introducing an electron attracting group as $R^5$or $R^6$, the electron density on N of $NR^5R^6$ decreases, thereby preventing coordination on the central M. $R^7$ is selected from $C_1$–$C_{10}$ alkyl groups, $C_1$–$C_{10}$ halogenated alkyl groups, $C_4$–$C_{20}$ aryl groups and $C_4$–$C_{20}$ halogenated aryl groups. Of these, a $C_1$–$C_{10}$ fluorinated alkyl groups is preferable. Due to the presence of an electron-attracting halogenated alkyl group as $R^7$, the negative charge of the central M is dissipated. Since this increases the electrical stability of the anion of the general formula (1), ion dissociation becomes extremely easy resulting in an increase of the ionic metal complex in solvent solubility, ion conductivity and catalyst activity. In addition, other properties of heat resistance, chemical stability and hydrolysis resistance are also improved. The case in which the halogenated alkyl group as $R^7$ is a fluorinated alkyl group in particular results in even greater advantageous effects.

In the general formula (1), the values of the constants m and n relating to the number of the above-mentioned ligands depend on the type of the central M. In fact, m is preferably from 1 to 3, while n is preferably from 0 to 4.

Next, the following provides an explanation of the process for synthesizing the ionic metal complex of the present invention. As a result of earnest studies, the synthesis process broadly divided into three types (i.e., the above-mentioned first, second and third processes) were found to obtain the target compound, the ionic metal complex.

As stated above, the first process for synthesizing the ionic metal complex comprises reacting a compound represented by the general formula (2) with a metal complex represented by the general formula (3). Symbols other than $R^8$ in the general formulas (2) and (3) are the same as those of the general formula (1). In fact, $R^8$ is selected from halogens, hydroxyl group, hydrogen atom, $C_1$–$C_{10}$ alkyl groups, $C_1$–$C_{10}$ halogenated alkyl groups, $C_4$–$C_{20}$ aryl groups, $C_4$–$C_{20}$ halogenated aryl groups and $X^3R^9$. Furthermore, $R^9$ is selected from $C_1$–$C_{10}$ alkyl groups, $C_1$–$C_{10}$ halogenated alkyl groups, $C_4$–$C_{20}$ aryl groups and $C_4$–$C_{20}$ halogenated aryl groups, and $X^3$ is O, S or $NR^5R^6$.

Mixing 1 mole of the compound represented by the general formula (2) with 1/m moles, where m is defined as in the general formula (3), of the metal complex represented by the general formula (3) results in addition of the active hydrogens (i.e., hydrogens respectively bonded to $X^1$ and O in the general formula (2)) of the compound of the general formula (2) to $R^8$ of the general formula (3), followed by dissociation in the form of $R^8H$. With this, the target ionic metal complex of the general formula (1) is obtained.

As stated above, the second process for synthesizing the ionic metal complex comprises:

(a) reacting a first compound represented by the general formula (2) with a metal complex represented by the general formula (4), thereby obtaining an intermediate; and (b) reacting the intermediate with a second compound, thereby obtaining the ionic metal complex.

The first compound contains at least two active hydrogens, as shown in the general formula (2). The second compound contains a cation represented by $A^{a+}$ that is a metal ion or onium ion. The second compound is selected from the group consisting of metal halides, metal alkoxides, metal carboxylates, metal hydroxides, metal oxides, metal carbonates, quaternary alkylonium halides, quaternary alkylonium hydroxides and quaternary alkylonium carboxylates. The symbols used in the formulas (2) and (4) are the same as those used in the general formulas (1) and (3). Mixing 1 mole of the first compound of the general formula (2) with 1/m moles of the second compound of the general formula (4) results in addition of the active hydrogens of the first compound of the general formula (2) to $R^8$ of the general formula (4), followed by dissociation in the form of $R^8H$. However, the number of $R^8$, that is, "2m−1" is deficient by one in the general formula (4), as compared with the number of active hydrogens in the general formula (2). Therefore, the surplus active hydrogen turns into a hydrogen ion (proton), and another active hydrogen that has formed a pair with the surplus active hydrogen is bonded to M. With this, there is obtained an intermediate represented by the general formula (1) wherein $A^{a+}$ is the proton. Then, this intermediate is reacted with the second compound containing $A^{a+}$ that is a metal ion or onium ion to conduct an ion-exchange between the proton of the intermediate and $A^{a+}$ of the second compound, thereby obtaining the ionic metal complex.

As stated above, the third process for synthesizing the ionic metal complex comprises:

(a) reacting a first compound represented by the general formula (2) with a second compound containing an alkali metal or alkali-earth metal, thereby obtaining an intermediate; and (b) reacting the intermediate with a metal complex represented by the general formula (5).

Symbols in the formulas (2) and (5) are the same as those of the general formula (1) with the exception of $R^{10}$. In fact, $R^{10}$ represents a halogen or hydroxyl group. By the step (a), active hydrogens of the first compound in an amount of 1 mole can be replaced with the alkali metal or alkali-earth metal of the second compound. The resulting intermediate can be mixed with the metal complex in an amount of 1/m moles to conduct the step (b). With this, the alkaline metal or alkaline earth metal ions of the intermediate are added to $R^{10}$ of the metal complex, followed by dissociation of the alkaline metal salt or alkaline earth metal salt of $R^{10}$ having low solubility in the form of precipitate. Thus, the target ionic metal complex of the general formula (1) is obtained.

Solvent can be used in the above-mentioned first, second and third processes, and it is not particularly limited as long as it can dissolve the raw materials even in minute amounts. The solvent is preferably an inert solvent, which does not react with compounds in the reaction system. Furthermore, the solvent is preferably one having a dielectric constant of at least 2. The use of a solvent having no dissolving power whatsoever is not preferable, since the reaction proceeds extremely slowly. Even if the solvent has only slight solubility, since the solubility of the target ionic metal complex is extremely large, the reaction proceeds rapidly. Examples of the solvent that can be used in the first, second and third processes include carbonates, esters, ethers, lactones, nitriles, amides, sulfones, alcohols and aromatics, and these solvents can either be used alone or in the form of a mixed solvent of two or more types. Specific examples of the solvent include propylene carbonate, ethylene carbonate, diethyl carbonate, dimethyl carbonate, methylethyl carbonate, dimethoxyethane, acetonitrile, propionitrile, tetrahydrofuran, 2-methyltetrahydrofuran, dioxane, nitromethane, N,N-dimethylformamide, dimethylsulfoxide, sulfolane, γ-butyrolactone, toluene, ethanol, methanol and water.

The first, second third processes can be conducted at a reaction temperature of −80° C. to 100° C., preferably 0° C. to 80° C. The reaction may not proceed sufficiently at a temperature lower than −80° C. Decomposition of the raw materials may occur at a temperature above 100° C. A temperature range of 0° C. to 80° C. is optimum in order to obtain a sufficient reaction rate while also preventing the occurrence of decomposition.

Since many of the raw materials used in the first, second and third processes are hydrolytic, it is preferable to carry out them in an atmosphere of air, nitrogen or argon and so forth having a low moisture content.

The following nonlimitative examples are illustrative of the present invention.

EXAMPLE 1

In a glove box having an atmosphere of a dew point of −50° C, 20.2 g of hexafluoro-2-hydroxyisobutyric acid (HOC(CF$_3$)$_2$COOH) were dissolved in 20 ml of dimethyl carbonate. Next, 6.8 g of lithium tetrakis(methoxy)borate (LiB(OCH$_3$)$_4$) were slowly added to this solution. After this addition, the solution was heated to 60° C. and allowed to react for 3 hours. Dimethyl carbonate was removed from the resulting reaction solution under a reduced pressure condition of 170° C. and 1 torr, thereby obtaining 20.0 g of a white solid as a product. This product was identified by NMR spectrum and elementary analysis as being LiB(OC(CF$_3$)$_2$COO)$_2$ having the following formula.

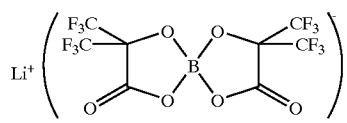

The NMR spectrum of the product is shown below.

$^{19}$F-NMR (hexafluorobenzene standard, solvent: CD$_3$CN); 88.1 ppm (6F, q, J=8 Hz); 88.3 ppm (6F, q, J=8 Hz); $^{11}$B-NMR (B(OCH$_3$)$_3$ standard, solvent: CD$_3$CN); −8.5 ppm (s).

EXAMPLE 2

10.0 g of hexafluoro-2-hydroxyisobutyric acid (HOC(CF$_3$)$_2$COOH) were dissolved in 20 ml of acetonitrile. Next, 3.4 g of triethylborate (B(OC$_2$H$_5$)$_3$) were slowly added to this solution. After this addition, the solution was heated to 80° C. and allowed to react for 3 hours while stirring. 3.5 g of hydroxytetraethyl ammonium ((C$_2$H$_5$)$_4$NOH) were added to the resulting reaction solution, and after stirring at 80° C. the solvent, acetonitrile, and by-products, water and ethanol, were removed under a reduced pressure condition of 170° C. and 1 torr, thereby obtaining 10.3 g of a white solid as a product. This product was identified by NMR spectrum and elementary analysis as being (C$_2$H$_5$)$_4$NB(OC(CF$_3$)$_2$COO)$_2$.

The NMR spectrum of the product is shown below.

$^{19}$F-NMR (hexafluorobenzene standard, solvent: CD$_3$CN); 88.1 ppm (6F, q, J=8 Hz); 88.3 ppm (6F, q, J=8 Hz); $^{11}$B-NMR (B(OCH$_3$)$_3$ standard, solvent: CD$_3$CN); −8.5 ppm (s).

EXAMPLE 3

10.0 g of hexafluoro-2-hydroxyisobutyric acid (HOC(CF$_3$)$_2$COOH) were dissolved in 20 ml of acetonitrile. Next, 1.5 g of boric acid (B(OH$_3$)) were slowly added to this solution. After this addition, the solution was heated to 60°

C. and allowed to react for 3 hours while stirring. 1.0 g of lithium chloride were added to the resulting reaction solution, and after stirring at 80° C. the solvent, acetonitrile, and a by-product, water, were removed under a reduced pressure condition of 170° C. and 1 torr, thereby obtaining 10.3 g of a white solid as a product. This product was identified by NMR spectrum and elementary analysis as being $LiB(OC(CF_3)_2COO)_2$.

The NMR spectrum of the product is shown below.

$^{19}$F-NMR (hexafluorobenzene standard, solvent: $CD_3CN$); 88.1 ppm (6F, q, J=8 Hz); 88.3 ppm (6F, q, J=8 Hz); $^{11}$B-NMR ($B(OCH_3)_3$ standard, solvent: $CD_3CN$); −8.5 ppm (s).

EXAMPLE 4

In a glove box having an atmosphere of a dew point of −50° C., 10.0 g of hexafluoro-2-hydroxyisobutyric acid ($HOC(CF_3)_2COOH$) were dissolved in 20 ml of dimethyl carbonate. Next, a lithium methoxide/methanol solution containing 3.6 g of lithium methoxide ($LiOCH_3$) was slowly added to this solution. The dimethyl carbonate and methanol were removed under a reduced pressure condition of 40° C. and 1 torr, thereby obtaining $LiOC(CF_3)_2COOLi$ as a product. After suspending this compound in acetonitrile, 2.2 g of $LiBF_4$ were added to this solution, followed by heating to 60° C. and allowing to react for 10 hours. After filtering the LiF precipitate that formed during the reaction, the acetonitrile was removed under a reduced pressure condition of 170° C. and 1 torr, thereby obtaining 10.3 g of a white solid as a product. This product was identified by NMR spectrum and elementary analysis as being $LiB(OC(CF_3)_2COO)_2$.

The NMR spectrum of the product is shown below.

$^{19}$F-NMR (hexafluorobenzene standard, solvent: $CD_3CN$); 88.1 ppm (6F, q, J=8Hz); 88.3 ppm (6F, q, J=8 Hz); $^{11}$B-NMR ($B(OCH_3)_3$ standard, solvent: $CD_3CN$); −8.5 ppm (s).

EXAMPLE 5

In a glove box having an atmosphere of a dew point of −50° C., 10.0 g of hexafluoro-2-hydroxyisobutyric acid ($HOC(CF_3)_2COOH$) were dissolved in 20 ml of dimethyl carbonate. Next, a lithium methoxide/methanol solution containing 3.6 g of lithium methoxide ($LiOCH_3$) was slowly added to this solution. The dimethyl carbonate and methanol were removed under a reduced pressure condition of 60° C. and 1 torr, thereby obtaining $LiOC(CF_3)_2COOLi$ as a product. After dissolving this compound in acetonitrile, 4.4 g of $LiBF_4$ were added to this solution, followed by heating to 60° C. and allowing to react for 10 hours. After filtering the LiF precipitate that formed during the reaction, the dimethyl carbonate was removed under a reduced pressure condition of 80° C. and 1 torr, thereby obtaining 12.5 g of a white solid as a product. This product was identified by NMR spectrum and elementary analysis as being $LiBF_2(OC(CF_3)_2COO)$ having the following formula.

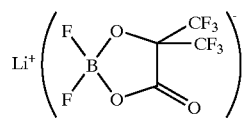

The NMR spectrum of the product is shown below.

$^{19}$F-NMR (hexafluorobenzene standard, solvent: $CD_3CN$); 15.3 ppm (2F, s); 88.2 ppm (6F, s); $^{11}$B-NMR (B(OCH3)$_3$ standard, solvent: $CD_3CN$); −14.1 ppm(t, J=4 Hz).

EXAMPLE 6

In a glove box having an atmosphere of a dew point of −50° C., 10.0 g of trifluorolactic acid ($HOCH(CF_3)COOH$) were dissolved in 20 ml of dimethyl carbonate. Next, 4.9 g of lithium tetrakis(methoxy)borate ($LiB(OCH_3)_4$) were slowly added to this solution. After this addition, the solution was heated to 60° C. and allowed to react for 3 hours. Dimethyl carbonate was removed from the resulting reaction solution under a reduced pressure condition of 170° C. and 1 torr, thereby obtaining 10.4 g of a white solid as a product. This product was identified by NMR spectrum and elementary analysis as being $LiB(OCH(CF_3)COO)_2$.

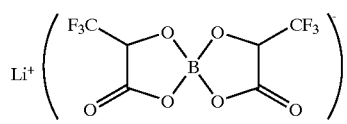

The NMR spectrum of the product is shown below.

$^{19}$F-NMR (hexafluorobenzene standard, solvent: $CD_3CN$); 87.12 ppm (3F, d, J=8 Hz); 87.18 ppm (3F, d, J=8 Hz); 87.32 ppm (3F, d, J=8 Hz).

Since the raw material, trifluorolactic acid, is a racemic modification having two types of optical isomers, three types of peaks were observed in $^{19}$F-NMR due to three combinations of (R,R), (S,S) and (R,S).

$^1$H-NMR; 4.57 ppm (1H, q, J=8 Hz); $^{11}$B-NMR ($B(OCH_3)_3$ standard, solvent: $CD_3CN$); −8.03 ppm (s).

EXAMPLE 7

In a glove box having an atmosphere of a dew point of −50° C., 4.2 g of 4,4,4-trifluoro-3-hydroxy-3-(trifluoromethyl)butyric acid ($HOC(CF_3)_2CH_2COOH$) were dissolved in 20 ml of dimethyl carbonate. Next, 1.3 g of lithium tetrakis(methoxy)borate ($LiB(OCH_3)_4$) were slowly added to this solution. After this addition, the solution was heated to 60° C. and allowed to react for 10 hours. Dimethyl carbonate was removed from the resulting reaction solution under a reduced pressure condition of 120° C. and 1 torr, thereby obtaining 4.3 g of a white solid as a product. This product was identified by NMR spectrum and elementary analysis as being $LiB(OC(CF_3)_2CH_2COO)_2$.

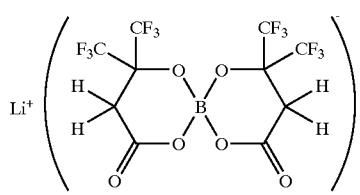

The NMR spectrum of the product is shown below.

$^{19}$F-NMR (hexafluorobenzene standard, solvent: $CD_3CN$); 85.0 ppm (12F, s); $^1$H-NMR; 2.86 ppm (2H, d, J=16 Hz); 2.75 ppm (2H, d, J=16 Hz).

What is claimed is:

1. An ionic metal complex represented by the general formula (1):

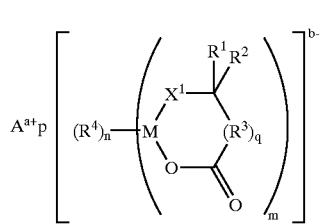

(1)

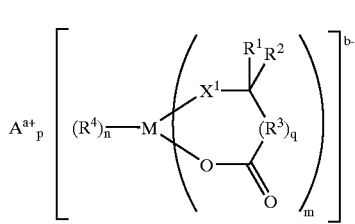

(1)

wherein:

M is a transition metal selected from the group consisting of elements of groups 3–11 of the periodic table, or an element selected from the group consisting of elements of groups 12–15 of the periodic table;

$A^{a+}$ represents a metal ion, onium ion or proton; provided that M is not B when $A^{a+}$ is $Cs^+$;

a represents a number from 1 to 3;

b represents a number from 1 to 3;

p is b/a;

m represents a number from 1 to 3;

n represents a number from 0 to 4;

q is 0 or 1;

$X^1$ represents O, S or $NR^5R^6$;

each of $R^1$ and $R^2$ independently represents a halogen, or $C_1$–$C_{10}$ halogenated alkyl group;

$R^3$ represents a $C_1$–$C_{10}$ alkylene group, $C_1$–$C_{10}$ halogenated alkylene group, $C_4$–$C_{20}$ aryl group or $C_4$–$C_{20}$ halogenated aryl group;

$R^4$ represents a halogen, $C_1$–$C_{10}$ alkyl group, $C_1$–$C_{10}$ halogenated alkyl group, $C_4$–$C_{20}$ aryl group, $C_4$–$C_{20}$ halogenated aryl group or $X^2R^7$;

$X^2$ represents O, S or $NR^5R^6$;

each of $R^5$ and $R^6$ represents H or a $C_1$–$C_{10}$ alkyl group; and $R^7$ represents a $C_1$–$C_{10}$ alkyl group, $C_1$–$C_{10}$ halogenated alkyl group, $C_4$–$C_{20}$ aryl group or $C_4$–$C_{20}$ halogenated aryl group.

2. An ionic metal complex according to claim 1, wherein said M is an element selected from the group consisting of Al, B, V, Ti, Si, Zr, Ge, Sn, Cu, Y, Zn, Ga, Nb, Ta, Bi, P, As, Sc, Hf, and Sb.

3. An ionic metal complex according to claim 2, wherein said M is an element selected from the group consisting of Al, B and P.

4. An ionic metal complex according to claim 1, wherein said $A^{a+}$ is a lithium ion, quaternary alkylammonium ion or proton.

5. An ionic metal complex according to claim 1, wherein said $A^{a+}$ is a lithium ion, proton, triphenylmethyl ion, trialkylammonium ion or metallocenium ion.

6. An ionic metal complex according to claim 1, wherein at least one of said $R^1$ and said $R^2$ is a fluorinated alkyl group.

7. An ionic metal complex according to claim 6, wherein said fluorinated alkyl group is trifluoromethyl group.

8. An ionic metal complex according to claim 1, wherein said $R^3$ is such that a chelate ring containing said M in the general formula (1) is a closed loop of bonded atoms of 5–10 in number.

9. An ionic metal complex according to claim 1, wherein said $R^7$ is a $C_1$–$C_{10}$ fluorinated alkyl group.

10. A process for synthesizing an ionic metal complex represented by the general formula (1):

wherein M is a transition metal selected from the group consisting of elements of groups 3–11 of the periodic table, or am element selected from the group consisting of elements of groups 12–15 of the period table; $A^{a+}$ represents a metal ion, onium ion or proton; provided that M is not B when $A^{a+}$ is $Cs^+$; a represents a number from 1 to 3; b represents a number from 1 to 3; p is b/a; m represents a number from 1 to 3; n represents a number from 0 to 4; q is 0 or 1; $X^1$ represents O, S or $NR^5R^6$; each of $R^1$ and $R^2$ independently represents H, a halogen, a $C_1$–$C_{10}$ alkyl group or $C_1$–$C_{10}$ halogenated alkyl group; $R^3$ represents a $C_1$–$C_{10}$ alkylene group, $C_1$–$C_{10}$ halogenated alkylene group, $C_4$–$C_{20}$ aryl group or $C_4$–$C_{20}$ halogenated aryl group; $R^4$ represents a halogen, $C_1$–$C_{10}$ alkyl group, $C_1$–$C_{10}$ halogenated alkyl group, $C_4$–$C_{20}$ aryl group, $C_4$–$C_{20}$ halogenated aryl group or $X^2R^7$; $X^2$ represents O, S or $NR^5R^6$; each of $R^5$ and $R^6$ represents H or a $C_1$–$C_{10}$ alkyl group; and $R^7$ represents a $C_1$–$C_{10}$ alkyl group, $C_1$–$C_{10}$ halogenated alkyl group, $C_4$–$C_{20}$ aryl group or $C_4$–$C_{20}$ halogenated aryl group, said process comprising reacting a compound represented by the general formula (2) wherein H represents active hydrogen with a metal complex represented by the general formula (3),

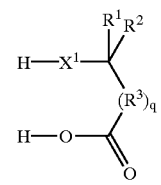

(2)

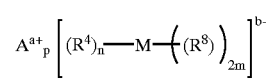

(3)

wherein $X^1$, $R^1$, $R^2$, $R^3$, $R^4$, M, $A^{a+}$, q, a, b, p, m, and n are defined as above, $R^8$ represents a halogen, hydroxyl group, hydrogen, $C_1$–$C_{10}$ alkyl group, $C_1$–$C_{10}$ halogenated alkyl group, $C_4$–$C_{20}$ aryl group, $C_4$–$C_{20}$ halogenated aryl group or $X^3R^9$; $X^3$ represents O, S or $NR^5R^6$ where $R^5$ and $R^6$ are defined as above; and $R^9$ represents a $C_1$–$C_{10}$ alkyl group, $C_1$–$C_{10}$ halogenated alkyl group, $C_4$–$C_{20}$ aryl group or $C_4$–$C_{20}$ halogenated aryl group.

11. A process according to claim 10, wherein said reacting is conducted in a solvent having a dielectric constant of at least 2.

12. A process according to claim 10, wherein said reacting is conducted at a temperature from 0 to 80° C.

13. A process for synthesizing an ionic metal complex represented by the general formula (1):

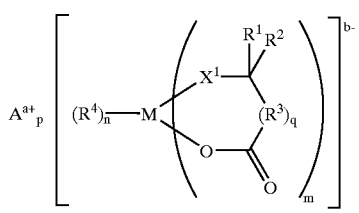

(1)

wherein M is a transition metal selected from the group consisting of elements of groups 3–11 of the periodic table, or an element selected from the group consisting of elements of groups 12–15 of the period table; $A^{a+}$ represents a metal ion or onium ion; provided that M is not B when $A^{a+}$ is $Cs^+$; a represents a number from 1 to 3; b represents a number from 1 to 3; p is b/a; m represents a number from 1 to 3; n represents a number from 0 to 4; q is 0 or 1; $X^1$ represents O, S or $NR^5R^6$; each of $R^1$ and $R^2$ independently represents H, a halogen, a $C_1$–$C_{10}$ alkyl group or $C_1$–$C_{10}$ halogenated alkyl group; $R^3$ represents a $C_1$–$C_{10}$ alkylene group, $C_1$–$C_{10}$ halogenated alkylene group, $C_4$–$C_{20}$ aryl group or $C_4$–$C_{20}$ halogenated aryl group; $R^4$ represents a halogen, $C_1$–$C_{10}$ alkyl group, $C_1$–$C_{10}$ halogenated alkyl group, $C_4$–$C_{20}$ aryl group, $C_4$–$C_{20}$ halogenated aryl group or $X^2R^7$; $X^2$ represents O, S or $NR^5R^6$; each of $R^5$ and $R^6$ represents H or a $C_1$–$C_{10}$ alkyl group; and $R^7$ represents a $C_1$–$C_{10}$ alkyl group, $C_1$–$C_{10}$ halogenated alkyl group, $C_4$–$C_{20}$ aryl group or $C_4$–$C_{20}$ halogenated aryl group, said process comprising:

reacting a first compound represented by the general formula (2) wherein H represents active hydrogen with a metal complex represented by the general formula (4), thereby obtaining an intermediate; and reacting said intermediate with a second compound, said second compound containing a cation represented by $A^{a+}$ defined as above and being selected from the group consisting of metal halides, metal alkoxides, metal carboxylates, metal hydroxides, metal oxides, metal carbonates, quaternary alkylonium hydroxides and quaternary alkylonium carboxylates, thereby obtaining said ionic metal complex,

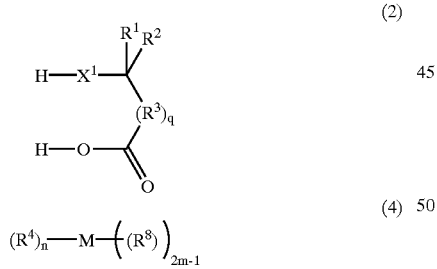

(2)

(4)

wherein $X^1$, $R^1$, $R^2$, $R^3$, $R^4$, M, q, m and n are defined as above, $R^8$ represents a halogen, hydroxyl group, hydrogen, $C_1$–$C_{10}$ alkyl group, $C_1$–$C_{10}$ halogenated alkyl group, $C_4$–$C_{20}$ aryl group, $C_4$–$C_{20}$ halogenated aryl group or $X^3R^9$; $X^3$ represents O, S or $NR^5R^6$ where $R^5$ and $R^6$ are defined as above; and $R^9$ represents a $C_1$–$C_{10}$ alkyl group, $C_1$–$C_{10}$ halogenated alkyl group, $C_4$–$C_{20}$ aryl group, or $C_4$–$C_{20}$ halogenated aryl group.

14. A process according to claim 13, wherein said reacting is conducted in a solvent having a dielectric constant of at least 2.

15. A process according to claim 13, wherein said reacting is conducted at a temperature from 0 to 80° C.

16. A process for synthesizing an ionic metal complex represented by the general formula (1):

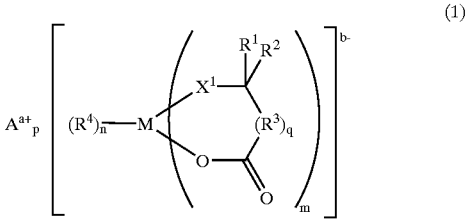

(1)

wherein M is a transition metal selected from the group consisting of elements of groups 3–11 of the periodic table, or an element selected from the group consisting of elements of groups 12–15 of the periodic table; $A^{a+}$ represents a metal ion, onium ion or proton; provided that M is not B when $A^{a+}$ is $Cs^+$; a represents a number from 1 to 3; b represents a number from 1 to 3; p is b/a; m represents a number from 1 to 3; n represents a number from 0 to 4; q is 0 or 1; $X^1$ represents O, S or $NR^5R^6$; each of $R^1$ and $R^2$ independently represents H, a halogen, a $C_1$–$C_{10}$ alkyl group or $C_1$–$C_{10}$ halogenated alkyl group; $R^3$ represents a $C_1$–$C_{10}$ alkylene group, $C_1$–$C_{10}$ halogenated alkylene group, $C_4$–$C_{20}$ aryl group or $C_4$–$C_{20}$ halogenated aryl group; $R^4$ represents a halogen, $C_1$–$C_{10}$ alkyl group, $C_1$–$C_{10}$ halogenated alkyl group, $C_4$–$C_{20}$ aryl group, $C_4$–$C_{20}$ halogenated aryl group or $X^2R^7$; $X^2$ represents O, S or $NR^5R^6$; each of $R^5$ and $R^6$ represents H or a $C_1$–$C_{10}$ alkyl group; and $R^7$ represents a $C_1$–$C_{10}$ alkyl group, $C_1$–$C_{10}$ halogenated alkyl group, $C_4$–$C_{20}$ aryl group or $C_4$–$C_{20}$ halogenated aryl group, said process comprising:

reacting a first compound represented by the general formula (2) with a second compound containing an alkali metal or alkali-earth metal, thereby obtaining an intermediate; and reacting said intermediate with a metal complex represented by the general formula (5),

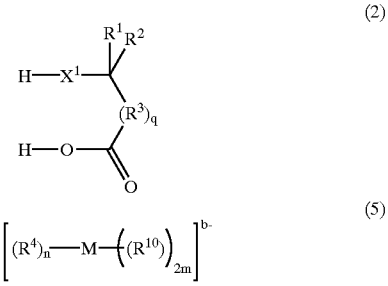

(2)

(5)

wherein $X^1$, $R^1$, $R^2$, $R^3$, $R^4$, M, $A^{a+}$, q, a, b, p, m, and n are defined as above, $R^{10}$ represents a halogen or hydroxyl group.

17. A process according to claim 16, wherein said reacting is conducted in a solvent having a dielectric constant of at least 2.

18. A process according to claim 16, wherein said reacting is conducted at a temperature from 0 to 80° C.

* * * * *